(12) United States Patent
Giera et al.

(10) Patent No.: US 10,408,852 B2
(45) Date of Patent: Sep. 10, 2019

(54) AUTOMATED CONTROL OF MICROFLUIDIC DEVICES BASED ON MACHINE LEARNING

(71) Applicant: Lawrence Livermore National Security, LLC, Livermore, CA (US)

(72) Inventors: Brian Giera, Oakland, CA (US); Eric Duoss, Dublin, CA (US); Du Nguyen, Fremont, CA (US); William Smith, Oakland, CA (US); Sachin Subhash Talathi, Pleasanton, CA (US); Aaron Creighton Wilson, Livermore, CA (US); Congwang Ye, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 157 days.

(21) Appl. No.: 15/498,282

(22) Filed: Apr. 26, 2017

(65) Prior Publication Data
US 2018/0311663 A1 Nov. 1, 2018

(51) Int. Cl.
*G01N 35/00* (2006.01)
*G05B 13/02* (2006.01)
(Continued)

(52) U.S. Cl.
CPC .. *G01N 35/00871* (2013.01); *B01L 3/502784* (2013.01); *G01N 15/00* (2013.01);
(Continued)

(58) Field of Classification Search
CPC ............. B01L 3/5027; B01L 2200/143; B01L 2200/0605; B01L 2300/023;
(Continued)

(56) References Cited

U.S. PATENT DOCUMENTS

| 5,715,182 A * | 2/1998 | Asai ....................... G01N 15/14 702/22 |
| 8,429,212 B1 * | 4/2013 | Bengio ............. G06F 17/30244 707/732 |

(Continued)

FOREIGN PATENT DOCUMENTS

| FR | 2567290 A1 | 1/1986 |
| WO | 2010007210 A1 | 1/2010 |

OTHER PUBLICATIONS

International Search Report and Written Opinion of International Application No. PCT/US2018/017699; dated Apr. 16, 2018; 13 pages.
(Continued)

*Primary Examiner* — Christopher E. Everett
(74) *Attorney, Agent, or Firm* — Perkins Coie LLP

(57) ABSTRACT

A system is provided to automatically monitor and control the operation of a microfluidic device using machine learning technology. The system receives images of a channel of a microfluidic device collected by a camera during operation of the microfluidic device. Upon receiving an image, the system applies a classifier to the image to classify the operation of the microfluidic device as normal, in which no adjustment to the operation is needed, or as abnormal, in which an adjustment to the operation is needed. When an image is classified as normal, the system may make no adjustment to the microfluidic device. If, however, an image is classified as abnormal, the system may output an indication that the operation is abnormal, output an indication of a needed adjustment, or control the microfluidic device to make the needed adjustment.

34 Claims, 4 Drawing Sheets

(51) Int. Cl.
    *G05D 7/06* (2006.01)
    *B01L 3/00* (2006.01)
    *G01N 15/00* (2006.01)
(52) U.S. Cl.
    CPC ..... *G01N 35/00623* (2013.01); *G05B 13/027* (2013.01); *G05D 7/0635* (2013.01); *G05D 7/0694* (2013.01); *B01L 2200/0652* (2013.01); *B01L 2200/143* (2013.01); *G01N 2035/00643* (2013.01); *G01N 2035/00881* (2013.01)
(58) Field of Classification Search
    CPC ....... G01N 35/00871; G01N 35/00623; G01N 2035/00881; G01N 2035/00643; G05D 7/0635; G05B 13/027
    See application file for complete search history.

(56) References Cited

U.S. PATENT DOCUMENTS

| | | | | |
|---|---|---|---|---|
| 9,552,549 | B1* | 1/2017 | Gong | G06N 3/084 |
| 9,739,783 | B1* | 8/2017 | Kumar | G01N 33/57492 |
| 2009/0005254 | A1* | 1/2009 | Griffiths | B01F 3/0807 |
| | | | | 506/7 |
| 2010/0119154 | A1* | 5/2010 | Taylor | G06K 9/00127 |
| | | | | 382/190 |
| 2011/0000560 | A1* | 1/2011 | Miller | B01L 3/0241 |
| | | | | 137/561 R |
| 2011/0229545 | A1* | 9/2011 | Shum | B01F 3/0807 |
| | | | | 424/409 |
| 2011/0285042 | A1* | 11/2011 | Viovy | B01J 13/04 |
| | | | | 264/4.3 |
| 2013/0064862 | A1* | 3/2013 | Weitz | A01N 25/28 |
| | | | | 424/400 |
| 2014/0026968 | A1* | 1/2014 | Abate | B01L 3/502784 |
| | | | | 137/1 |
| 2014/0272984 | A1 | 9/2014 | Hasson et al. | |
| 2015/0347817 | A1* | 12/2015 | Valvik | G06K 9/00127 |
| | | | | 382/133 |
| 2016/0063359 | A1* | 3/2016 | Szegedy | G06K 9/66 |
| | | | | 382/158 |
| 2016/0086785 | A1* | 3/2016 | Chiu | H01J 49/0445 |
| | | | | 250/282 |
| 2016/0140425 | A1* | 5/2016 | Kulkarni | G06K 9/4628 |
| | | | | 382/159 |
| 2016/0231324 | A1* | 8/2016 | Zhao | C12Q 1/6816 |
| 2016/0279068 | A1* | 9/2016 | Utech | A61K 9/1652 |
| 2016/0370266 | A1* | 12/2016 | White | B01L 3/502761 |
| 2017/0056331 | A1* | 3/2017 | Stone | A61K 31/085 |
| 2017/0242234 | A1* | 8/2017 | Ashcroft | G01N 15/1436 |
| 2017/0333903 | A1* | 11/2017 | Masaeli | B01L 3/502715 |
| 2018/0032801 | A1* | 2/2018 | Gur | G06K 9/00362 |
| 2018/0056288 | A1* | 3/2018 | Abate | B01L 3/0268 |
| 2018/0169024 | A1* | 6/2018 | Lee | A61P 19/04 |
| 2018/0195945 | A1* | 7/2018 | Schneider | G03H 1/02 |
| 2018/0320150 | A1* | 11/2018 | Chaput | C12N 9/1252 |

OTHER PUBLICATIONS

Squires, T.M. and Quake, S.R., "Microfluidics: Fluid Physics at the Nanoliter Scale," Reviews of Modern Physics, vol. 77, Jul. 2005, pp. 977-1026.

Karpathy, A. et al., "large-Scale Video Classification with Cnovolutional Neural Networks," http://cs.stanford.edu/people/karpathy/deepvideo, 2014, 8 pages.

Wu, J. and Gu, M., "Microfluidic Sensing: State of the Art Fabrication and Detection Techniques," J. Biomed. Opt. 16 (8), 080901, Aug. 4, 2011.

Utada, A. S. et al., "Monodisperse Double Emulsions Generated from a Microcapillary Device," Science, Apr. 22, 2005, vol. 308, iss. 5721, pp. 537-541.

Nabavi, S.A. et al., "Double Emulsion Production in Glass Capillary Microfluidic Device: Parametric Investigation of Droplet Generation Behaviour," Chemical Engineering Science, vol. 130, 2015, pp. 183-196.

Vericella, J. J. et al., "Encpsulated Liquid Sorbents for Carbon Dioxide Capture," Nat. Commun. 6:6124 doi: 10.1038/ncomms7124 (2015).

* cited by examiner

AUTOMATED CONTROL OF MICROFLUIDIC DEVICES BASED ON MACHINE LEARNING

STATEMENT REGARDING FEDERALLY SPONSORED RESEARCH

The United States government has rights in this invention pursuant to Contract No. DE-AC52-07NA27344 between the U.S. Department of Energy and Lawrence Livermore National Security, LLC, for the operation of Lawrence Livermore National Laboratory.

BACKGROUND

Microfluidic systems or devices, such as inkjet print heads, DNA microarrays, biosensors, cell sorting devices, and lab-on-a-chip devices, rely on sub-millimeter plumbing components to manipulate fluids precisely. A microfluidic system includes various channels, also referred to as capillaries, through which fluids are processed, such as by moving, mixing, and separating the fluids. A microfluidic system may include various components, such as micropumps and microvalves, to control the processing. A micropump may be used to deliver fluids in a continuous or pulsed manner to a channel. A microvalve may be used to control flow rate and direction of fluids entering a channel.

Due to the low Reynolds flow characteristics within microfluidic channels, microfluidic systems are amendable to physics-based models that inform suitable geometric designs and/or operating conditions for a wide variety of microfluidic applications. In one application, microfluidic systems have been used to produce droplets containing an inner fluid that are microencapsulated by a middle (or shell) fluid and that are formed in the presence of and transported by an outer fluid. The fluids are immiscible. As the droplets of the inner fluid are formed, they are surrounded by the middle fluid. Such a microfluidic system may employ a double-capillary junction. (See, Utada, A. S., Lorenceau, E., Link, D. R., Kaplan, P. D., Stone, H. A., and Weitz, D. A., "Monodisperse Double Emulsions Generated from a Microcapillary Device," Science, Apr. 22, 2005, vol. 308, iss. 5721, pp. 537-541, which is hereby incorporated by reference.) A double-capillary junction may consist of a square glass capillary that encompasses a tapered capillary and a uniformly cylindrical capillary, whose openings are separated by a gap. Using independently controlled syringe pumps, the middle fluid and the outer fluid are fed from opposite directions into the square capillary, and the inner fluid is fed into the tapered capillary. The tapered capillary is centered on an orifice of the cylindrical capillary (i.e., formation channel). The inner, middle, and outer fluids enter the cylindrical capillary via the center, middle, and outer portion, respectively, of the orifice. Under ideal operating conditions characterized by a "dripping" regime, as the three fluids exit via the cylindrical capillary, the middle fluid encapsulates the inner fluid and pinches off into droplets near the orifice that are swept downstream by the outer fluid. The middle fluid may be a photopolymerizable silicone that hardens when exposed to an ultraviolet light source that is placed downstream of droplet formation to form the microcapsules. Within the dripping regime, nearly monodisperse microcapsules form at rates of 1-100 Hz with tunable diameters ranging from 100-600 micrometers, depending on fluid viscosities, flow rates, and capillary sizes.

The efficient operation of a microfluidic system, especially for large-scale production campaigns, typically requires time intensive monitoring and intervention by humans to prevent or minimize disruptions in production that occur when a system enters a mode of abnormal operation (e.g., the middle fluid is not properly encapsulating the droplet) due to abnormalities in fluid flow. The abnormalities in fluid flow that may cause a disruption may include unexpected clogs, air bubbles, chemical impurities, particulates, pressure fluctuations in external pumps, fluid instabilities, and so on. Such disruptions may result in time and material loss, reduced production, reduced quality, and, depending on the severity, even damage to the microfluidic system. To minimize the effects of such disruptions, a person may use a microscope to view the fluid flow of the microfluidic system to assess the cause of the disruption. Depending on the cause, the person can then make various adjustments to the operation of the microfluidic system, such as adjusting the flow rate of a fluid, to return to normal operation. Because the operation requires human monitoring and intervention, the identification of the abnormalities and the determination of needed adjustments are both subjective and time-consuming, which may result in considerable loss of production, especially when the person is not highly experienced. In addition, a large-scale production environment may require highly parallelized arrays of microfluidic platforms that may be too complex to be effectively monitored and controlled by humans.

DETAILED DESCRIPTION

Figure 1:
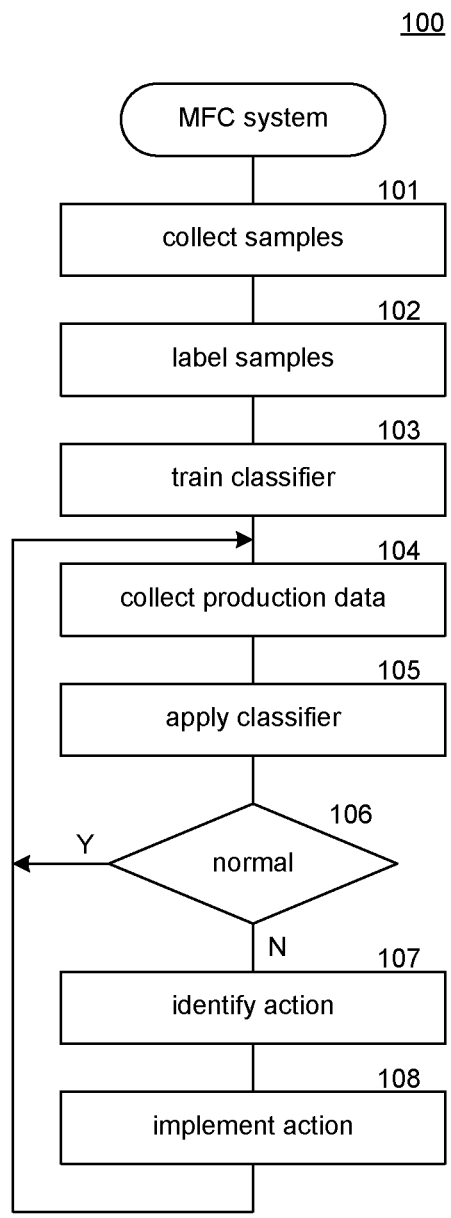
FIG. 1 is a flow diagram that illustrate the overall processing of an MFC system in some embodiments.

A method and a system are provided to automatically monitor and control the operation of a microfluidic device using machine learning technology. In some embodiments, a microfluidic control ("MFC") system receives images of a channel of a microfluidic device collected by a camera during operation of the microfluidic device. Upon receiving an image, the MFC system applies a classifier to the image to classify the operation of the microfluidic device as normal in which no adjustment to the operation is needed, or as abnormal in which an adjustment to the operation is needed. The classifier may include a convolution neural network ("CNN") that is trained using images collected during operation of a microfluidic device and is manually labeled as representing a normal or an abnormal mode of operation. During operation of the microfluidic device, when an image is classified as normal, the MFC system may make no adjustment to the microfluidic device. If, however, an image is classified as abnormal, the MFC system may output an indication that the operation is abnormal, output an indication of a needed adjustment, or control the microfluidic device to make the needed adjustment. In this way, the MFC system provides an automated way to monitor and control the operation of a microfluidic device to quickly respond to and correct abnormal operations in a consistent and objective manner. Moreover, the MFC system can be used to monitor and control a highly parallelized operation of microfluidic devices.

In some embodiments, the MFC system may be used to monitor and control the operation of a microfluidic device that is producing microcapsules using a double emulsion. The classifier of the MFC system may be used to classify the operation not only as normal or abnormal, but also as one of three modes of abnormal operation. During normal operation, the microfluidic device may be considered to be in a "dripping" regime in which the microcapsules are being properly formed. During abnormal operation, the microfluidic device may be considered to be in a "jetting," "breaking," or "wetting" regime. When the microfluidic device transitions from the dripping regime to a non-dripping regime, the droplet formation may be non-uniform or may not occur at all. The causes of a transition to a non-dripping regime may include clogs, bubbles, pressure fluctuations, viscosity changes within the photo-curable or other fluids, and so on. In the jetting regime, inertial forces exceed surface tension that cause aspherical, polydisperse, and/or double droplets to form farther into the capillary, leading to suboptimal microcapsules. In the breaking regime, the middle fluid poorly emulsifies/coats the inner fluid, and the droplets break. In the wetting regime, the inner fluid breaks through the middle fluid and wets the cylindrical channel, making droplet formation impossible. When in each of the abnormal regimes, the MFC system may adjust the flow rate of one or more fluids until the operation transitions to the dripping regime. When in the breaking regime, the MFC system may make no adjustments initially and if the operation does not self-correct by transitioning to the dripping regime, the flow rate may be adjusted and may turn off the ultraviolet light to prevent microcapsule formation.

In some embodiments, the MFC system may interface with camera and microscope position to collect images of junction of a microfluidic device where droplet might form. During a training phase, images are collected during operation of the microfluidic device. A person who is monitoring and controlling the microfluidic device records when the microfluidic device transitions between regimes. The person may also identify adjustments and adjust the microfluidic device to return the operation to the dripping regime. Each image may be automatically labeled based on the regime that was recorded when the image was collected. Alternatively, a person may subsequently review and label each image individually, which may provide a labeling that is more accurate than the automatic labelling. The classifier is then trained using the training data. To verify the accuracy of the classifier, a portion of the labeled images may be excluded from the training data to be used as test data during cross-validation of the classifier. After the classifier is trained, the classifier is used to classify the images of the test data. The accuracy of the classifier can then be assessed based on the labels assigned to the images during classification and the labels assigned when the training data was labeled. The accuracy of the classifier may suffer, for example, because of "overfitting," resulting from an inadequate number or inadequate diversity of images for a certain regime.

In some embodiments, the classifier may include a CNN followed by a sub-classifier, such as a support vector machine or a linear regression classifier. The CNN is used to learn significant features of the training data and their corresponding weights. The sub-classifier is used to learn a function that divides the features into the various regimes. During operation, an image is input to the CNN to extract the learned features of the image, and the features are input to the sub-classifier to assign a label indicating the regime. Alternatively, the CNN itself may assign a label without the need for a separate sub-classifier. The CNN may include multiple convolution layers. Each convolution layer convolves small regions of the image using a kernel (or multiple kernels) to generate an activation for each region based on weights of neurons of the convolution layer learned during training. The activations may then be non-linearly transformed by a rectified linear unit ("ReLU"), and have their dimensions reduced using max pooling techniques before being input into the next convolution layer. The last layer may be fully connected in the sense that each activation that is input is connected to each neuron of the last layer. The activations of the last layer may be used as the features that are input to the sub-classifier to assign a label to the input image. The sub-classifier may also input features other than those extracted by the CNN. For example, the temperature or impedance of the fluid in a channel may be collected and provided as a feature to the sub-classifier. To speed up the training process, the classifier may be pre-trained using labeled images that are unrelated to microfluidics. For example, the classifier may be trained using images collected and labeled as part of the ImageNet project. The complexity of the CNN may be selected based on a tradeoff between computational complexity and labeling accuracy. For example, if a more accurate labeling is desired, the number of layers (fully connected or not), kernels, neurons, and so on can be increased, but at an increased computational expense.

In some embodiments, the MFC system may maintain a mapping of labels to procedures for adjusting a microfluidic device to return to a normal operation from a mode of abnormal operation as indicated by an assigned label. The procedures may vary from simple adjustments of a single parameter to complex adjustments controlled by a stored procedure (e.g., computer code) that is executed to adjust multiple controls of the microfluidic device simultaneously. A simple adjustment may specify to lower the flow rate by X amount every 10 seconds. A stored procedure when executed may input controllable parameters (e.g., the current flow rate of each fluid and the temperature of the fluid in the channel), non-controllable parameters (e.g., impedance of fluid in the channel), and history of adjustments, and apply an algorithm to identify the next adjustment, such as increase flow rate of the inner fluid by X, decrease flow rate of the outer fluid by Y, and decrease the temperature by Z. The procedures for adjusting can be customized to the particular microfluidic device, its current function (e.g., creating certain microcapsules), the types of the fluids, and so on.

Although the MFC system has been described as being used to make adjustments to the operation of a microfluidic device, the MFC system has other uses. For example, the MFC system may be used to sort cells of a target shape into a target bin and all other cells into another bin. To support such a use, a classifier may be trained to recognize cells of the target shape from the images of the training data. During operation, upon detecting a cell of the target shape, the MFC system may control a microswitch to direct a cell of the target shape into the target bin. As another example, during production of microcapsules, the MFC system may be used to control the microfluidic device to deliver well-formed microcapsules to one bin and malformed microcapsules to another bin, regardless of whether the MFC system is used to control the production of the microcapsules. As another example, the MFC system may be used to monitor and control a micromixer, which mixes two or more fluids within a microchannel. For example, a micromixer may be used to mix different reactants or small amounts of acids or bases to neutralize the pH of a fluid. Because of the small dimensions of the microchannels of a micromixer, it can be difficult to achieve the desired mixing. The MFC system may be used to adjust flow rate to achieve the desired mixing. The MFC system may determine whether the desired mixing has been achieved based on analysis of the images and/or sensor data. For example, when a red fluid and a white fluid are mixed as desired, the mixture will be pink. Also, a pH sensor may be used to ensure the desired pH has been achieved.

FIG. 1 is a flow diagram that illustrates the overall processing of an MFC system in some embodiments. An MFC system 100 trains a classifier and then employs the classifier to control the operation of a microfluidic device. In block 101, the MFC system collects sample images during operation of a training microfluidic device. The training microfluidic device may be the same type (e.g., manufacturer, architecture, and dimensions) of microfluidic devices that are to be controlled during production. The MFC system may also collect non-image training data such as temperature, impedance, conductivity, and pH. (See, Wu, J. and Gu, M., "Microfluidic Sensing: State of the Art Fabrication and Detection Techniques," J. Biomed. Opt. 16(8), 080901, Aug. 4, 2011.) In block 102, the MFC system collects labels for the sample images. For example, a person may manually label each image as dripping, jetting, breaking, and wetting for the production of microcapsules. Additional labels may be used to further refine abnormal operation of the production of microcapsules. Also, different sets of labels would be used for different types of microfluidic devices, for production of different products, and so on. In block 103, the MFC system trains the classifier using the labeled sample images. Since the training may be computationally expensive, the training may be performed on a powerful computing system, such as a cloud-based system, using many computers with graphic processing units, a massively parallel computing system, and so on. In blocks 104-108, the MFC system loops, monitoring and controlling the operation of a microfluidic device during production. In block 104, the MFC system collects production data that includes an image of the production channel and any of the non-image data used for training. In block 105, the component applies a classifier to the production data. The classifier assigns one of the labels to the production data. In decision block 106, if the assigned label indicates that the microfluidic device is operating normally, then the MFC system loops to block 104 to collect the next production data, else the MFC system continues at block 107. In block 107, the MFC system identifies an action (e.g., decrease flow rate of a fluid) that should be taken to control the microfluidic device to return to normal operation. In decision block 108, the MFC system controls the microfluidic device based on the identified action and then loops to block 104 to select the next production data.

Figure 2:
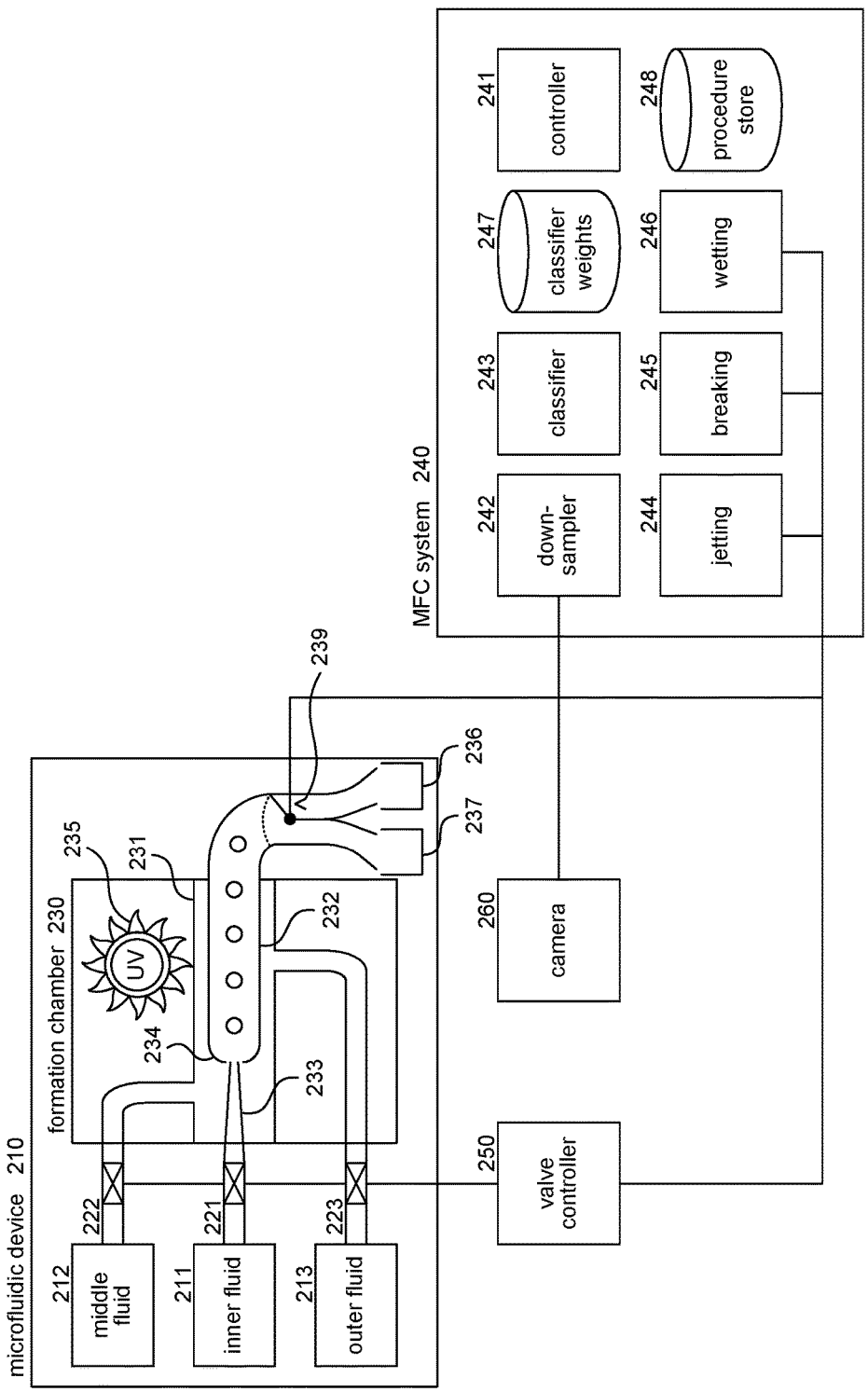
FIG. 2 is a block diagram that illustrates components of the MFC system in some embodiments.

FIG. 2 is a block diagram that illustrates components of the MFC system in some embodiments. An MFC system 240 interfaces with a valve controller 250 for controlling a microfluidic device 210. The MFC system also interfaces with a camera 260 that collects images of the formation channel during operation of the microfluidic device. The microfluidic device includes an inner fluid container 211, a middle fluid container 212, and an outer fluid container 213. The containers are connected to a formation chamber 230 via capillaries controlled by microvalves 221, 222, and 223. The valve controller controls the flow rate of the microvalves. The formation chamber includes an outer capillary 231 that includes a tapered capillary 233 and a formation channel 232. The middle fluid and outer fluid are injected into the outer capillary at opposite ends. The inner fluid is injected via the tapered capillary. The formation channel includes an orifice 234 through which the fluids enter. The formation chamber may also include an ultraviolet light source 235 for hardening of the middle fluid as a shell for droplets of the inner fluid. The microfluidic device may also include a switch 239 for controlling the microcapsules formed in the formation channel to be diverted to either bin 236 or bin 237. For example, during a disruption in the formation of the microcapsules, the MFC system may control the switch to divert the malformed microcapsules into a discard bin, rather than a production bin. The MFC system includes a controller 241, a downsampler 242, a classifier 243, a jetting component 244, a breaking component 245, and a wetting component 246. The MFC system also includes a classifier weight store 247 and a procedure store 248. The controller controls the overall operation of the MFC system. When an image is collected from the camera, the downsampler component is invoked to optionally downsample the image. The classifier is then invoked to assign a label to the downsampled image. The classifier weight store stores the weights of the CNN that were learned during the training of the classifier. The jetting component, breaking component, and wetting component are invoked when the microfluidic device is in the corresponding regime to control the return to the dripping regime. The procedure store stores various procedures for returning the microfluidic device to normal operation.

The components of the MFC system may execute on computing systems that may include a central processing unit, input devices, output devices (e.g., display devices and speakers), storage devices (e.g., memory and disk drives), network interfaces, graphics processing units, accelerometers, cellular radio link interfaces, global positioning system devices, and so on. The input devices may include keyboards, pointing devices, touch screens, gesture recognition devices (e.g., for air gestures), head and eye tracking devices, microphones for voice recognition, and so on. The computing systems may include desktop computers, laptops, tablets, e-readers, personal digital assistants, smartphones, gaming devices, servers, and so on. The learning system may execute on servers of a data center, massively parallel systems, and so on. The computing systems may access computer-readable media that include computer-readable storage media and data transmission media. The computer-readable storage media are tangible storage means that do not include a transitory, propagating signal. Examples of computer-readable storage media include memory such as primary memory, cache memory, and secondary memory (e.g., DVD) and other storage. The computer-readable storage media may have recorded on it or may be encoded with computer-executable instructions or logic that implements components of the MFC system. The data transmission media is used for transmitting data via transitory, propagating signals or carrier waves (e.g., electromagnetism) via a wired or wireless connection.

The MFC system may be described in the general context of computer-executable instructions, such as program modules and components, executed by one or more computers, processors, or other devices. Generally, program modules or components include routines, programs, objects, data structures, and so on that perform particular tasks or implement particular data types. Typically, the functionality of the program modules may be combined or distributed as desired in various examples. Aspects of the MFC system may be implemented in hardware using, for example, an application-specific integrated circuit (ASIC).

Figure 3:
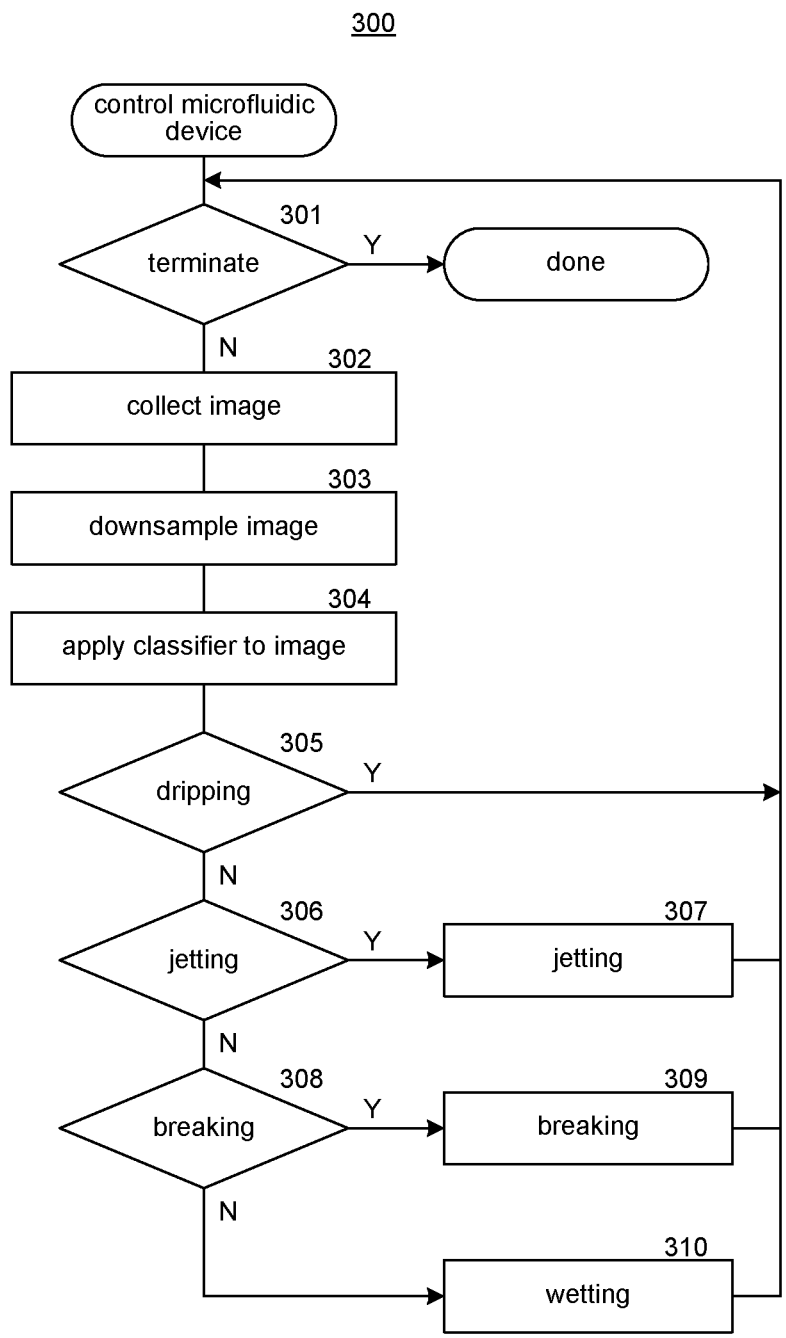
FIG. 3 is a flow diagram that illustrates a controller for a microfluidic device in some embodiments.

FIG. 3 is a flow diagram that illustrates a controller for a microfluidic device in some embodiments. A control microfluidic device component 300 is invoked to control the operation of a microfluidic device. In decision block 301, if the controlling of the microfluidic device has terminated, then the component completes, else the component continues at block 302. In block 302, the component collects an image from the camera. In block 303, the component downsamples the image. The amount of downsampling may factor in a trade-off between computational expense and accuracy of the labeling. In block 304, the component applies the classifier to the image to assign a label. In decision block 305, if the assigned label is dripping, then the component loops to block 301 to process the next image, else the component continues at block 306. In decision block 306, if the assigned label is jetting, then the component continues at block 307, else the component continues at block 308. In block 307, the component invokes the jetting component to control the return to the dripping regime from the jetting regime and then loops to block 301. In decision block 308, if the assigned label is breaking, then the component continues at block 309, else the component continues at block 310. In block 309, the component invokes the breaking component to control the return to the dripping regime from the breaking regime and then loops to block 301. In block 310, the component invokes the wetting component to control the return to the dripping regime from the wetting regime and then loops to block 301.

Figure 4:
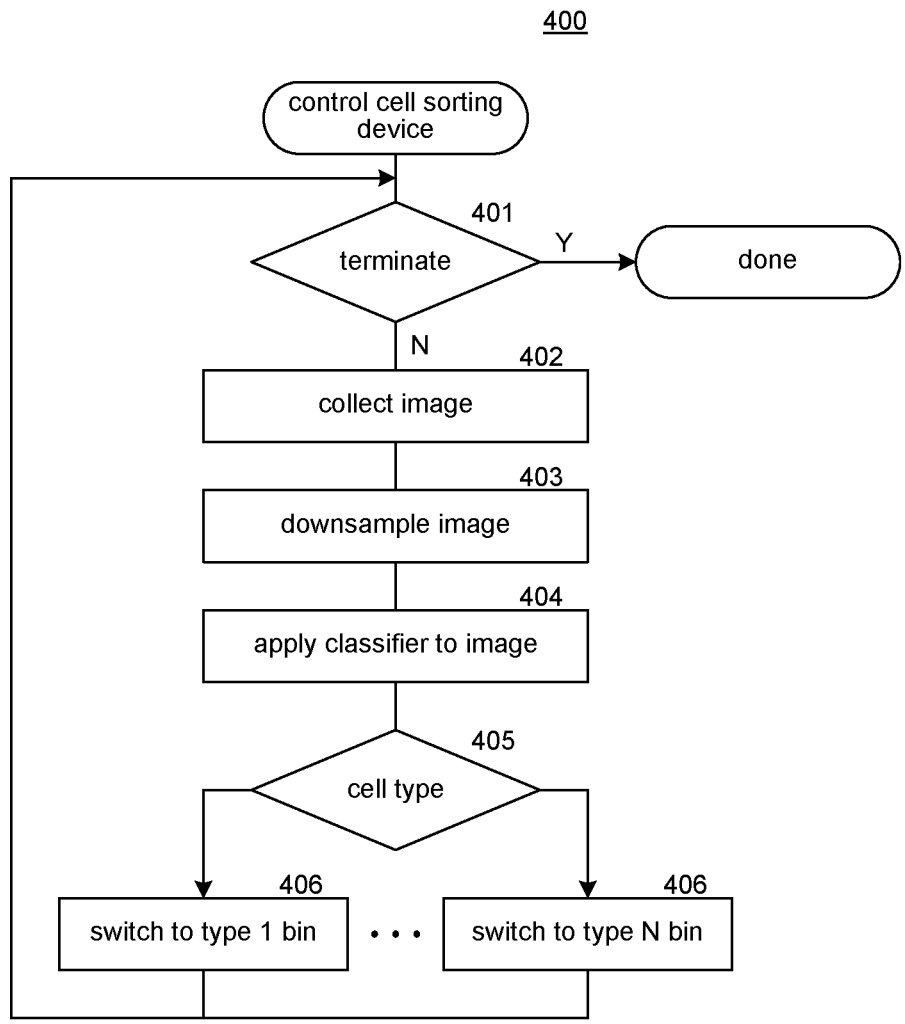
FIG. 4 is a flow diagram that illustrates the processing of a control cell sorting device component in some embodiments.

FIG. 4 is a flow diagram that illustrates the processing of a control cell sorting device component in some embodiments. A control cell sorting device component 400 may be invoked to control a cell sorting device to sort the cells into various bins based on the cell type assigned by a classifier. In decision block 401, if the cell sorting is to be terminated, then the component completes, else the component continues at block 402. In block 402, the component collects an image from the camera. In block 403, the component downsamples the image. In block 404, the component applies the classifier to the image to assign a label indicating the cell type represented by the image. In decision block 405, depending on the cell type, the component continues to the appropriate component 406. In blocks 406, the components switch the sorting to direct the cell of the image into the appropriate bin for the type of cell and then loops to block 401.

The following paragraphs describe various embodiments of aspects of the MFC system. An implementation of the MFC system may employ any combination of the embodiments. The processing described below may be performed by a computing device with a processor that executes computer-executable instructions stored on a computer-readable storage medium that implements the MFC system.

A method performed by a computing system is provided. For each of a plurality of intervals, the method receives an image of a channel of a microfluidic device and applies a classifier to the image to generate a label for the image. When the label indicates that the microfluidic device is operating abnormally, that method identifies an adjustment for controlling the microfluidic device to transition to operating normally. In some embodiments, the method controls the microfluidic device based on the adjustment. In some embodiments, the adjustment indicates a change in flow rate of a fluid. In some embodiments, the fluids of the channel are a double emulsion. In some embodiments, the classifier is trained using training data that includes sample images that each have a label, the sample images being of a channel of a training microfluidic device taken during operation of the training microfluidic device. In some embodiments, the labels comprise dripping, jetting, breaking, and wetting. In some embodiments, the classifier is pre-trained based on images that are not of the channel. In some embodiments, the classifier includes a convolution neural network. In some embodiments, the classifier includes a convolution neural network to generate features of the image and a sub-classifier to generate the label for the image based on the generated features of the image. In some embodiments, the sub-classifier is a support vector machine. In some embodiments, the sub-classifier generates the label for the image further based on an additional feature not generated by the convolution neural network.

In some embodiments, a computing system is provided that includes one or more computer-readable storage media storing computer-executable instructions and one or more processors for executing the computer-executable instructions stored in the one or more computer-readable storage media. The instructions, when executed, control the computing device to receive images of a channel of a fluidic device during operation of the fluidic device. For each image, the instructions, when executed, control the computing device to apply a classifier to the image to generate a label for the image, and when the label indicates to adjust the operation of the fluidic device, control the fluidic device to adjust the operation of the fluidic device in accordance with the label. In some embodiments, the fluidic device is adjusted to sort items traveling through the channel. In some embodiments, the fluidic device is used to sort cells. In some embodiments, the fluidic device is used for microencapsulation. In some embodiments, a label indicates an abnormal operation of the fluidic device. In some embodiments, when a label indicates an abnormal operation, the flow rate of a fluid that enters the fluidic device is adjusted. In some embodiments, the classifier includes a convolution neural network. In some embodiments, the classifier is trained using training data that includes sample images that each have a label. The sample images are of a channel of a training fluidic device taken during operation of the training fluidic device.

In some embodiments, a method performed by a computing system is provided. For each of a plurality of intervals, the method receives an image of a channel of a microfluidic device during operation of the microfluidic device. The method also applies a classifier to the image to assign one of a plurality of labels to the image. The classifier includes a convolution neural network that was trained using training data that includes sample images that each have a label. The sample images are of a channel of a training microfluidic device taken during operation of the training microfluidic device. When the label is associated with an adjustment for the microfluidic device, the method identifies the adjustment and controls operation of the microfluidic device based on the adjustment. In some embodiments, an adjustment is a change in flow rate of a fluid of a double emulsion. In some embodiments, an adjustment is to discard malformed droplets of a double emulsion. In some embodiments, during initial operation of the microfluidic device, the adjustments control the microfluidic device to enter a normal mode of operation. In some embodiments, the microfluidic device is a micromixer device. In some embodiments, the microfluidic device is a microencapsulation device.

Although the subject matter has been described in language specific to structural features and/or acts, it is to be understood that the subject matter defined in the appended claims is not necessarily limited to the specific features or acts described above. Rather, the specific features and acts described above are disclosed as example forms of implementing the claims. For example, the MFC system may be used to control fluidic devices that may not technically be considered to be "micro" fluidic. Also, the MFC system may use machine learning techniques that do not employ a CNN. For example, a technique may be used to extract features of the images that are deemed to be relevant to determining whether a fluidic device is operating normally or abnormally. When the MFC system is used to monitor a micromixer, a feature may be the color of the mixture, measures of color variations within the mixture, and so on. The extracted feature can be used to train a support vector machine, a linear regression classifier, a neural network, and so on based on labels assigned to the images and non-image data collected from sensors (e.g., pH sensors and mass spectrometers). Accordingly, the invention is not limited except as by the appended claims.

We claim:

1. A method performed by a computing system, the method comprising, for each of a plurality of intervals:
receiving an image of a channel of a microfluidic device;
applying a classifier to the image to generate a label for the image; and
when the label indicates that the microfluidic device is operating abnormally, identifying an adjustment for controlling the microfluidic device to transition to operating normally
wherein the labels comprise dripping, jetting, breaking, and wetting.

2. The method of claim 1 further comprising controlling the microfluidic device based on the adjustment.

3. The method of claim 1 wherein the adjustment indicates a change in flow rate of a fluid.

4. The method of claim 1 wherein fluids of the channel are a double emulsion.

5. The method of claim 1 wherein the classifier is pre-trained based on images that are not of the channel.

6. The method of claim 1 wherein the classifier includes a convolution neural network.

7. The method of claim 1 wherein the classifier includes a convolution neural network to generate features of the image and a sub-classifier to generate the label for the image based on the generated features of the image.

8. The method of claim 7 wherein the sub-classifier is a support vector machine.

9. The method of claim 7 wherein the sub-classifier generates the label for the image further based on an additional feature not generated by the convolution neural network.

10. The method of claim 1 wherein the classifier being trained using training data that includes sample images that each has a label, the sample images being of a channel of a training microfluidic device taken during operation of the training microfluidic device.

11. A method performed by a computing system, the method comprising:
for each of a plurality of intervals,
receiving an image of a channel of a microfluidic device during operation of the microfluidic device;
applying a classifier to the image to assign one of a plurality of labels to the image, the classifier including a convolution neural network that was trained using training data that includes sample images that each have a label, the sample images being of a channel of a training microfluidic device taken during operation of the training microfluidic device; and
when the label is associated with an adjustment for the microfluidic device, identifying the adjustment; and
controlling operation of the microfluidic device based on the adjustment
wherein an adjustment is a change in a flow rate of a fluid of a double emulsion and an adjustment is to discard malformed droplets of a double emulsion.

12. The method of claim 11 wherein during initial operation of the microfluidic device, the adjustments control the microfluidic device to enter a normal mode of operation.

13. A method performed by a computing system, the method comprising, for each of a plurality of intervals:
receiving one image for that interval of a channel of a microfluidic device;
applying a classifier to the one image to generate a label for the one image the label indicating whether the microfluidic device is operating normally or abnormally; and
indicating that the microfluidic device is operating as specified by the label
wherein the operation of the microfluidic device for each interval can be determined from content of the one image for that interval.

14. The method of claim 13 further comprising adjusting operation of the microfluidic device based on the generated label.

15. The method of claim 14 wherein the adjusting is changing the flow rate of a fluid.

16. The method of claim 15 wherein fluids of the channel are a double emulsion.

17. The method of claim 13 wherein the labels comprise dripping, jetting, breaking, and wetting.

18. The method of claim 13 wherein the classifier includes a convolution neural network to generate features of the image and a sub-classifier to generate the label for the image based on the generated features of the image.

19. The method of claim 13 wherein the microfluidic device is used to sort cells.

20. The method of claim 13 wherein the microfluidic device is used for microencapsulation.

21. The method of claim 13 wherein the label indicates an abnormal operation of the microfluidic device.

22. The method of claim 21 wherein when the label indicates an abnormal operation, the flow rate of a fluid is adjusted.

23. The method of claim 13 wherein the classifier is trained using training data that includes sample images that each have a label, the sample images being of a channel of a training microfluidic device taken during operation of the training microfluidic device.

24. One or more computing systems comprising:
one or more computer-readable storage media storing computer-executable instructions that, when executed, control the one or more computing systems to, for each of a plurality of intervals:
receive one image for that interval of a channel of a microfluidic device;
apply a classifier to the one image to generate a label for the one image the label indicating whether the microfluidic device is operating normally or abnormally; and
indicate that the microfluidic device is operating as specified by the label wherein the operation of the microfluidic device for each interval can be determined from content of the one image for that interval and one or more processors for executing the computer-executable instructions stored in the one or more computer-readable storage media.

25. The one or more computing systems of claim 24 wherein the instructions further control the one or more computing systems to adjust operation of the microfluidic device based on the generated label.

26. The one or more computing systems of claim 25 wherein the adjusting is changing the flow rate of a fluid.

27. The one or more computing systems of claim 26 wherein fluids of the channel are a double emulsion.

28. The one or more computing systems of claim 24 wherein the labels comprise dripping, jetting, breaking, and wetting.

29. The one or more computing systems of claim 24 wherein the classifier includes a convolution neural network to generate features of the image and a sub-classifier to generate the label for the image based on the generated features of the image.

30. The one or more computing systems of claim 24 wherein the microfluidic device is used to sort cells.

31. The one or more computing systems of claim 24 wherein the microfluidic device is used for microencapsulation.

32. The one or more computing systems of claim 24 wherein the label indicates an abnormal operation of the microfluidic device.

33. The one or more computing systems of claim 32 wherein when the label indicates an abnormal operation, the flow rate of a fluid is adjusted.

34. The one or more computing systems of claim 24 wherein the classifier is trained using training data that includes sample images that each have a label, the sample images being of a channel of a training microfluidic device taken during operation of the training microfluidic device.

* * * * *